United States Patent [19]

Seibl et al.

[11] Patent Number: 6,001,610
[45] Date of Patent: Dec. 14, 1999

[54] METHOD FOR THE PARTICULARLY SENSITIVE DETECTION OF NUCLEIC ACIDS

[75] Inventors: Rudolf Seibl, Penzberg; Viola Rosemeyer, Wavre, both of Germany

[73] Assignee: Roche Diagnostics, GmbH, Mannheim, Germany

[21] Appl. No.: 09/020,538

[22] Filed: Feb. 9, 1998

Related U.S. Application Data

[62] Division of application No. 08/561,632, Nov. 22, 1995, Pat. No. 5,783,392.

[30] Foreign Application Priority Data

Nov. 23, 1994 [DE] Germany ............................ 44 41 626

[51] Int. Cl.[6] .............................. C12P 19/34; C12Q 1/68; C07H 21/02; C07H 21/04
[52] U.S. Cl. ............................ 435/91.2; 435/6; 435/875; 536/24.3; 536/24.33; 536/23.1; 935/77; 935/78
[58] Field of Search .............................. 435/6, 91.1, 91.2, 435/183, 875; 536/23.1, 24.3, 24.31, 24.33, 25.3; 436/94; 935/77

[56] References Cited

U.S. PATENT DOCUMENTS

| | | | |
|---|---|---|---|
| 4,945,368 | 7/1990 | Goodman et al. | 435/6 |
| 5,011,769 | 4/1991 | Duck et al. | 435/6 |
| 5,200,313 | 4/1993 | Carrico | 435/6 |
| 5,736,365 | 4/1998 | Walker et al. | 435/91.2 |
| 5,744,308 | 4/1998 | Guillou-Bonnici et al. | 435/6 |
| 5,744,311 | 4/1998 | Fraiser et al. | 435/6 |
| 5,824,517 | 10/1998 | Cleuziat et al. | 435/91.2 |

FOREIGN PATENT DOCUMENTS

| | | |
|---|---|---|
| 0 201 184 | 12/1986 | European Pat. Off. . |
| 0 329 822 | 8/1989 | European Pat. Off. . |
| WO 88/10315 | 12/1988 | WIPO . |
| WO 89/09284 | 10/1989 | WIPO . |
| WO 89/10415 | 11/1989 | WIPO . |

*Primary Examiner*—Stephanie Zitomer
*Attorney, Agent, or Firm*—Nikaido Marmestein Murray & Oram, LLP.

[57] ABSTRACT

A method of detecting a target nucleic acid A is disclosed, comprising hybridizing the target nucleic acid A with a probe nucleic acid B which contains a sequence B1 which base pairs with a part of the target nucleic acid A and a sequence B2, cleaving the hybridized probe nucleic acid B to produce a cleavage product B' containing the sequence B2, hybridizing the cleavage product B' with a template nucleic acid C containing a sequence C2 which base pairs with a part of the cleavage product B' and a sequence C1 which does not hybridize with the sequence B1 of the probe nucleic acid B, extending the hybridized cleavage product B' with an extension sequence B3 which is template-specific to a part of the sequence C1, hybridizing a probe D with the extension product, wherein the probe D contains a sequence D1 which base pairs with the extension sequence B3 and a sequence D2, and detecting any of the various products formed throughout the method. Products for performing the method are also disclosed.

10 Claims, 5 Drawing Sheets

METHOD FOR THE PARTICULARLY SENSITIVE DETECTION OF NUCLEIC ACIDS

This application is a Divisional of application Ser. No. 08/561,632, filed Nov. 22, 1995, now U.S. Pat. No. 5,783, 392, issued Jul. 21, 1998, which claims priority to DE 4441626.1, filed Nov. 23, 1994.

Subject matter of the invention is a method for the particularly sensitive detection of nucleic acids by hybridizing a probe nucleic acid with a target nucleic acid, digesting the hybridized part of the probe nucleic acid and detecting the cleavage product as well as a set of reagent suitable for this purpose.

After investigation had shown that the use of the specific information contained in nucleic acids could have enormous advantages in the recognition of infectious disease parameters and genetic conditions, investigators attempted to make nucleic acids the subject matter of assays. In many cases, such a detection method requires the amplification of nucleic acid sequences in order to generate a sufficient sensitivity in the assay procedure used. Investigators developed both methods for the amplification of a target sequence and methods for the amplification of a target sequence independent nucleic acid sequence. An example for the amplification of the target sequence is the polymerase chain reaction (PCR) as described in EP-A-0 201 184 where the two strands of the target nucleic acid are amplified in an in-vitro replication reaction. The reaction temperature is changed in cycles to denature a double-stranded target nucleic acid, to allow hybridization with the initiator molecules (primers) as well as the subsequent DNA synthesis (extension of the primers) and to repeat these steps. If all steps of the PCR are carried out in an optimal manner, the result is an exponential amplification of nucleic acids. In the practice, however, the amplification factor is often strongly reduced.

In-vitro transcriptions have also been used to amplify target sequences. An example for such a reaction is described in WO 88/10315. In this amplification reaction, two primers are used of which one contains the promoter sequence. As in the PCR, the primers are complementary to different strands of the sequence to be amplified. EP-A-0 329 822 describes an improvement of this method where the ribonucleic acids that were obtained by transcribing the double-stranded nucleic acid product, which in turn is an intermediate product, are digested in the hybrid, in order to allow hybridization of the newly synthesized DNA with a promoter-containing primer molecule. By digesting the originally formed transcripts, it is possible to form another double-stranded promoter-containing nucleic acid from each so-formed RNA molecules. These double-stranded promoter-containing nucleic acids are used for another transcription start.

As opposed to the above-described method, the target sequence-specific signal amplification is not used to amplify the nucleic acid to be detected, but instead concentrates on the specific identification of the target sequence. In order to accomplish this, a signal is amplified in dependency upon the presence of the target sequence. Such a method is described, for example, in WO 89/09284 and WO 89/10415. In this so-called cycling probe reaction (CPR), a labelled, chimeric DNA-RNA-DNA probe molecule is used which hybridizes with a target DNA molecule. The result of this hybridization is an RNA-DNA hybrid, which serves as a substrate for the RNAse H. As this enzyme specifically digests the RNA portion of the hybrid, the probe molecule is cleaved and the resulting fragments diffuse away from the target sequence due to the lower melting temperature. Subsequently, the target molecule can be hybridized with another probe molecule, and the cycle is repeated. The fragments of the probe molecule are detected via the labels adhering to it.

Subject matter of the invention is a method for the detection of nucleic acids, comprising the following steps a) target sequence-dependent generation of a multitude of primers and b) amplification of the primers or parts of the primers.

Another subject matter of the invention is a method for the amplification of short nucleic acid sequences with the aid of longer nucleic acid sequences containing said short nucleic acid sequences, a method for the sensitive detection of a target nucleic acid A and kits for the implementation of this method.

Target nucleic acids are understood to be nucleic acids which are to be detected either directly or indirectly. In the following text and especially in the drawing, the target nucleic acid is designated with the letter A. A method for the direct detection of target nucleic acids is understood to be a method where the nucleic acids are already provided for the procedural steps of the method in accordance with the invention. An indirect method is understood to be a method where the target nucleic acids are subject to pretreatment or are provided by means of pretreatment. Such pretreatment steps include isolation of the nucleic acids, treatment with reagents, e.g. restriction enzymes, or pre-amplification. Reverse transcription of RNA can also be considered a pretreatment. The target nucleic acid can, hence, be a nucleic acid of any desired origin, such as viral, bacterial or cellular nucleic acids. It can be provided in solution, suspension, but also be fixed to solid bodies or be contained in cell-containing media, cell smears, fixed cells, tissue sections, or fixed organisms. In a preferred manner, the nucleic acid is present in solution.

A complementary or homologous nucleic acid is one that can hybridize with the corresponding nucleic acid or hybridize with the nucleic acid that is complementary to the corresponding nucleic acid.

Usually, the first step in detection methods for nucleic acid is to make the target nucleic acid with the suitable reagents available. This may include changes in the pH (alkaline), heat, repetition of extreme temperature changes (freezing/thawing), changing the physiological growth conditions (osmotic pressure), effects of detergents, chaotropic salts or enzymes (e.g. proteases, lipases), either alone or in combination in order to release nucleic acids. Since the method of the invention is very sensitive and selective, it is also possible to detect small amounts of nucleic acids in the presence of other substances, such as proteins, cells, cell fragments, but also in the presence of nucleic acids that are not to be detected.

Suitable target nucleic acids are, for example, ribonucleic acids and deoxyribonucleic acids. The nucleic acids can also be modified, e.g. in preceding treatments. A particularly preferred target nucleic acid is the deoxyribonucleic acid (DNA).

The method of the invention is a special embodiment of a test that is based on an hybridization event, in particular target sequence-specific signal amplification. Tests that are based on hybridization events are basically known to the expert in the field of nucleic acid diagnostics. Unless experimental details are listed hereinafter, reference is made to the complete contents of "nucleic acid hybridization" edited by B. D. Hames and S. J. Higgins, IRL Press, 1986, e.g. in chapters 1 (Hybridization Strategy), 3 (Quantitative Analysis of Solution Hybridization) and 4 (Quantitative Filter Hybridization), Current Protocols in Molecular Biology, Edt. F. M. Ausubel et al., J. Wiley and Son, 1987, and Molecular Cloning, Edt. J. Sambrook et al., CSH, 1989. Other known methods include the preparation of labelled nucleoside triphosphates as described in U.S. Pat. No. 5,344,757, the chemical synthesis of modified and unmodified oligonucleotides, the cleavage of nucleic acids with the aid of restriction enzymes, the selection of hybridization conditions to achieve a desired specificity which depends among other things from the extent of the complementary between the nucleic acids to be hybridized, their GC contents and their lengths as well as the formation of nucleic acids from nucleoside triphosphates with the aid of polymerases, if necessary with the the aid of so-called primers.

A label as understood in the present invention is a directly or indirectly detectable group. Directly detectable groups are, for example, radioactive ($^{32}$P), dyed, or fluorescent groups or metal atoms. Indirectly detectable groups include immunologically or enzymatically active compounds such as antibodies, antigens, haptens, or enzymes or enzymatically active parts of enzymes. They are detected in a subsequent reaction or reaction sequence. Haptens are particularly preferred, as such labelled nucleoside triphosphates are particularly well suited as substrates of polymerases. The subsequent reaction with a labelled antibody to the hapten or the haptenized nucleoside is then rapidly done. Such nucleoside triphosphates include bromonucleoside triphosphates or digoxigenin, digoxin, biotin, or fluorescein-coupled nucleoside triphosphates. The steroids listed in EP-A-0 324 474 and their detection have proven to be particularly suitable. For the incorporation of nucleic acids, we refer to EP-A-0 324 474.

Nucleoside triphosphates (NTP) are ribo (rNTP)- or deoxyribo-nucleoside triphosphates (dNTP).

A characteristic feature of the present method is that a multitude of nucleic acids with a short sequence which function as primers can be generated from nucleic acids with a longer sequence with the aid of and in dependency upon the presence of the target nucleic acids. A longer sequence is understood to be a sequence that is by one or more, preferable 5–1000, particularly preferred 8–100, nucleobase units (e.g. mononucleotides) longer than the short nucleic acid. The short nucleic acid must satisfy two conditions. First, it must be able to form hybrids with nucleic acids via base-base interaction. Such sequences contain especially nucleic acids which consist of natural nucleotide components. The sequences can, however, also be nucleic acid analogs or modified nucleic acids, e.g. nucleic acids which still exhibit the hybridization properties of a nucleic acid, but no longer have a phosphate-sugar backbone or contain non-natural bases. Particularly suitable molecules are those described in U.S. Pat. No. 08/108,591 or U.S. Pat. No. 07/712,396. The second condition that the sequence must satisfy is its use as a primer in an extension reaction. Such extension reactions are in particular the polymerase-dependent extension of the primers by mononucleotide units with the aid of mononucleoside triphosphates. In such a reaction, the 3'-end of the primer, when hybridized with the template nucleic acid, is extended by mononucleotides, so that the extension product is essentially complementary to the corresponding site on the template nucleic acid.

The generation of the primers or short nucleic acids in accordance with the invention can be accomplished in any desired manner; cleavage of the longer nucleic acid, especially by partial enzymatic digestion of this nucleic acid is, however, preferred.

The primers generated in the step in accordance with the invention have a preferred length of more than 12 bases. The primers preferably contain a sequence of 12 to 35 bases, which is essential for the subsequent treatment of the primers (e.g. hybridization and enzymatic extension). Especially at their 5'-ends, the primers can contain numerous other nucleotides or non-nucleotide molecule parts, if desired.

In the second step of the method of the invention, the primers formed in the first part or parts thereof, e.g. a partial sequence, are amplified. In a preferred manner, the primer amplification procedure includes digestion of a longer molecule. In a particularly preferred manner, amplification is achieved by extension of a primer, e.g. to a longer sequence compared with the primer (short sequence), on a template nucleic acid C (to form a longer nucleic acid), hybridization of an amplification probe D with an extension product of the primer, and digestion (cleavage) of the amplification probe while generating a new primer molecule. Owing to the fact that the extension product of the primer is again available for cleaving an amplification probe, the number of primer molecules increases with each cleavage procedure. Moreover, the extension of the primers obtained through cleavage also leads to the formation of extension products which in turn are also available for cleaving an amplification probe.

Owing to the fact that the initial generation of a primer is target sequence-dependent, the amount of primer and/or extension products or other intermediate products generated, is a measure for the presence of target nucleic acids A in a sample.

The method of the invention is, hence, a method where a once generated extension product of a primer is again used for the cyclical generation of one or several primers and where a once generated primer is again used to generate an extension product.

A longer nucleic acid is understood to be a nucleic acid that contains an inactive primer part and a part which leads, if digested, to an activation of the primer. After activation of the primer, the latter is available for an extension reaction. One aspect of the invention is concerned with the amplification of short nucleic acids, especially primers, by digesting the longer nucleic acids while forming the primers. As understood in the present invention, the probe nucleic acids B are also such longer nucleic acids.

Short nucleic acids as understood in the invention are the digestion products of the above-mentioned longer nucleic acids. The short nucleic acids are in particular those nucleic acids which can also function as primers, i.e. the ones that can be extended by an extension segment.

Probe molecules B are molecules which contain two parts B1 and B2 that are linked to one another. Part B1 is characterized in that it can hybridize with the target nucleic acid or a part thereof. To accomplish this, the part must be sufficiently complementary. Moreover, it must be possible to cleave Part B1 when the latter is hybridized with the target nucleic acid. Digestion or cleavage is here understood to be the separation of part B1 in two or more no longer linked part or refers to cleaving part B1 from B2 while it is preferred that the target nucleic acid be not cleaved. Part B 1 can, hence, contain ribonucleotide or abasic sequences. In the preferred case, part B1 contains two, particularly preferred four or more monoribonucleotide units that are linked to each other as it is commonly known from nucleic acids, while the part of the nucleic acid which is complementary thereto is a deoxyribonucleic acid. In this case, probe nucleic acid B in part B1 can be cleaved in that the formed hybrid is brought into contact with RNAse H. If abasic sequences are present, digestion can be achieved with the aid of AP endonuclease.

When a sufficient degree of sensitivity is given, even the cleavage of the target nucleic acid may become acceptable, i.e. one primer instead of several is generated for each target molecule.

In this process, at least part of the hybridizable part B1 is cleaved. The result is a cleavage product B' which contains the nucleic acid-specific part B2 that cannot be cleaved in the hybrid of B with the target nucleic acid and which does preferably not hybridize with the target nucleic acid. It may also contain portions of part B1 which was originally hybridized with the target nucleic acid.

The conditions for the hybridization of the target nucleic acid with a probe nucleic acid are preferably selected such that a selective hybridization of the probe nucleic acid with the target nucleic acid via part B1 still occurs while unspecific hybridizing of the probe nucleic acid with other nucleic acids of the sample that are not to be detected do not occur. The fragments which are produced in the cleavage of the probe nucleic acid, including cleavage product B', are shorter than the original probe nucleic acid and will under the selected conditions no longer be able to form a stable hybrid with the target nucleic acid. They will, hence, release the target nucleic acid A under selected conditions. The latter is then available for hybridization with another probe nucleic acid.

The cleavage of the probe nucleic acid can also produce different fragments B' which contain either only part B2 or also remains of part B1. This depends on the conditions selected.

In the following text, a nucleic acid-specific part of the nucleic acid is understood to be a sequence which can hybridize with another sequence as the target nucleic acid with a specific hybridization occurring under the selected conditions; i.e. there is no hybridization relevant for the procedure with other nucleic acids present in the reaction mixture that are not involved in the respective reaction step. Typical nucleic acid-specific parts are parts B2 of the probe nucleic acid, part C2 of the template nucleic acid and part D2 of the amplification probe. The nucleic acid-specific part B2 of the probe nucleic acid which preferably does not hybridize with the target nucleic acid must satisfy the condition that it is not digested under the conditions selected for the target sequence-specific digestion of part B1. Moreover, it should be able to hybridize with the later-on defined template oligonucleotide. Principally, the sequence of part B2 can be selected as desired. It should, however, be taken into consideration that complementarity with the target nucleic acid makes hybridization of the cleavage product B' with the template oligonucleotide more difficult, which may lower the sensitivity as compared to optimal conditions. B2 can also be a ribonucleic acid, a deoxyribonucleic acid or a modified nucleic acid. If part B1 contains a ribonucleic acid and if cleavage is achieved with the aid of an RNAse, part B2 is preferably no ribonucleic acid that can be cleaved under these conditions, preferably it is a deoxyribonucleic acid. However, B2 can also be a ribonucleic acid that is modified such that it can no longer be cleaved by an RNAse. Another possibility is the use of nucleic acid analogs which still have the hybridization properties of the nucleic acid, but no longer contain the phosphate sugar chain portion or non-natural bases. Particularly suitable PNA molecules are described in U.S. Pat. No. 08/108,591 or other molecules like as described in U.S. Pat. No. 07/712,396. The preferred condition that this part should not hybridize with the target nucleic acid applies in particular to the conditions selected during the hybridization of the probe nucleic acid with the target nucleic acid. Part B2 is preferably selected such that it does not hybridize with nucleic acids that are contained in the sample, but are not to be detected. However, part B2 should contain a sequence able to hybridize with the template nucleic acid C. The conditions for the hybridization of the target nucleic acid with the probe nucleic acid and of the template nucleic acid with the cleavage product B' can be selected independently.

The template nucleic acid C in accordance with the invention contains a part C2 which can hybridize with the cleavage product B' and especially its nucleic acid-specific part B2 or a portion thereof and possibly with still present rests of B1. Suitable molecules for the template nucleic acid C are all those that allow such a hybridization, i.e. nucleic acids composed of natural nucleotide components. Nucleic acid analogs, however, consisting of non-naturally occurring components or containing such components and which can function as a template can also be used. Moreover, the template nucleic acid should be stable with respect to digestion under the conditions selected. If the probe nucleic acid is cleaved with an RNAse, the template nucleic acid is preferably a deoxyribonucleic acid. In addition to part C2, the template nucleic acid has a part C1 which cannot hybridize with part B1 or rests of B1 of the probe nucleic acid that may still be present. In a particularly preferred manner, this part C1 does not form stable hybrids with nucleic acids contained in the sample that are not to be detected and the target nucleic acid itself This part C1 is preferably located in 5'-direction from part C2.

The conditions must in any case ensure that the one or several cleavage products B' hybridize with the template nucleic acid such that B' hybridizes with the end generated during cleavage to the template nucleic acid.

In a subsequent step, hybrid consisting of cleavage product B' and template nucleic acid C is extended with a nucleic acid part B3 that is complementary to part C1. B' must hence also serve as a primer, i.e. it must be extendable at the 3'-end. This can be achieved in any desired manner, preferably, however, by means of enzymatic extension. A preferred enzymatic extension method is to link mononucleoside triphosphates in a condensation reaction using C1 as template nucleic acid. The conditions to be selected are known to the expert in the field. Extension can be carried out, for example, with the aid of a DNA polymerase of Thermus aquaticus according to U.S. Pat. No. 4,889,818. Preferred mononucleoside triphosphates are dNTPs. In this case, cleavage product B' acts as a primer and a short nucleic acid that is extended. Another possibility of enzymatic extension is the use of a ligase. Attention should be paid to the fact that the so-formed extension product is stable under the conditions selected for the cleavage of the probe nucleic acid. These conditions are satisfied if both the primer and the extension fragment are a DNA if an RNAse H is used to cleave the probe nucleic acid.

Under the conditions selected for the extension of the cleavage product B', possibly forming hybrids of uncleaved probe nucleic acid B and template nucleic acid C are not extended as the 3'-end of the probe nucleic acid, for example, does not hybridize with the template nucleic acid.

The extension of uncleaved probe nucleic acids B at the target nucleic acid as a template does not affect the generation of primers B' and can be prevented by blocking the 3'-end of the probe nucleic acid B, for example, by using a dideoxynucleotide as the last nucleotide.

In one embodiment of the method of the invention, amplification of the primer is achieved in that the formation of the segment B3 for hybridization of B3 with the amplification probe D is used for this purpose, preferably after denaturing the hybrid of template nucleic acid and primer B' extended by portion B3.

An amplification probe D is understood to be a nucleic acid which contains a part D1 which is either completely or partially complementary to B3, i.e. the part of the extension product of the primer (cleavage product B') generated via extension. This part which is now attached to the primer is referred to as B3. An essential characteristic of the amplification probe D is that it can be cleaved in its part D1. It is preferably configured such that the cleavage conditions for the amplification probe and the probe nucleic acid B are essentially identical with respect to the reagents used. D1 is therefore preferably also a ribonucleic acid. Moreover, the amplification probe D contains a part D2 which satisfies the conditions of a nucleic acid-specific sequence.

The particular amplification effect of the method is achieved in that the digestion of the amplification probe directly or indirectly leads to another cleavage product which can hybridize with a template nucleic acid and, hence, (as a primer) initiate another amplification cycle.

In addition, when appropriate conditions are selected, several amplification probes can bind successively one after another to each extension product obtained, so that several cleavage products are generated since the cleavage products, similar to the probe nucleic acid B, do not form a stable hybrid with the extension product.

When directly generated, the amplification probe is selected such that the additional part D2 is completely or partially complementary to C2 and, hence, essentially identical to the originally formed cleavage product B'. The cleavage product D' formed in the digestion reaction of D can, hence, again be used in an extension reaction with the aid of the nucleic acid C as template.

With respect to type and arrangement of parts D1 and D2, the amplification probe is subject to the conditions that apply to the probe nucleic acid B.

In an indirect method, the amplification probe D is selected such that it contains a nucleic acid-specific part D2 in addition to part D1; said part D2 is, however, not complementary to C2 and does not hybridize with other nucleic acids contained in the reaction mixture, except another template nucleic acid E, which contains a part E2 which can hybridize with D2 and a part E1 which acts as a template to extend D'. After hybridizing cleavage fragment D' with a second template nucleic acid E and extending the cleavage fragment and the primer by a part D3, said newly formed part D3 is available for cleaving another amplification probe F as does part B3, preferably after separation of the hybrid.

This amplification probe F in turn can contain a part F1 complementary to D3 and a nucleic acid-specific part F2. Cleavage in part F1 generates a cleavage product F' which acts identical to cleavage product D' or cleavage product B', depending on the sequence selected. The degree of amplification is further increased if the cleavage product is reintroduced in another extension/digestion cycle using additional template and amplification probes. The system of the invention is, hence, very flexible owing to the selection of the sequences of the nucleic acid-specific part in the probe nucleic acid and/or the amplification probes. As it is expected that an increasing number of probe and template nucleic acids also leads to a greater variety of diverse molecules, the complexity will increase with an increasing amount of different probe and/or template nucleic acids. It is, hence, preferred that part D2 of the amplification probe be complementary to C2 or a part thereof.

Thermal denaturing can be employed, for example, to separate the hybrids of template nucleic acid C and extension product of cleavage product B' and also the hybrids of template nucleic acids C or E and the extension product of cleavage product D' as well as possible additional hybrids (e.g. when additional template nucleic acids were used). Principally, however, it is also possible to employ non-thermal denaturing procedures.

The extension of uncleaved amplification probes, e.g. with the extension products, can be prevented by blocking the 3'-end of the amplification probe, e.g. by means of a dideoxynucleotide, as is done with probe nucleic acid B.

The temperature of the method of the invention is selected such that the activities of the enzymes used are optimized while the hybridization conditions still allow sufficient specificity. When non-thermostable RNAse is used, for example, an expedient temperature range is one between 30 and 60°, particularly preferred 42°. When a thermostable RNAse is used, it is also possible to work at higher temperatures. The temperature used for the extension reaction also depends on the enzyme used for the extension reaction. When thermostable enzymes are used, e.g. Taq-DNA-polymerase, a temperature range between 50 and 80° is preferred, particularly preferred is one at approximately 60–70°. By increasing the retention time of the enzymes at the sites of reaction, it should be possible to increase the reaction rates and therefore to lower the necessary action time or increase the sensitivity.

The template nucleic acid can be a circular molecule. In this case, it is preferred to use an extension enzyme with strand displacement activity.

The probe nucleic acid, the matrix nucleic acid, and the amplification nucleic acid can be obtained according to principally known methods as soon as the sequence of the parts has been determined. In a preferred case that an oligonucleotide of a length of less than 100 mononucleotide components is used, a synthesis according to commonly known chemical methods is preferred (e.g. solid-phase synthesis according to Merrifield). This also allows the simple synthesis of mixed oligonucleotides (RNA/DNA chimers). When longer nucleic acids are used, genetical engineering methods or chemical/enzymatic methods as described in U.S. Pat. No. 08/467,875 are preferred. Part B1 is preferably 12–35, part B2 preferably 15–50, part C1 is preferably 10–100 and part C2 15–50 nucleotides in length. The same applies to all other template nucleic acids and the amplification probes.

FIG. 1 shows a basic embodiment of the method of the invention, where part D2 of the amplification probe is complementary to part C2 of the template nucleic acid and where cleavage product D' is, hence, extended at the template nucleic acid C.

FIG. 2 is a diagrammatic representation of an embodiment where the cleavage product D' is hybridized with a new template nucleic acid E. A probe nucleic acid F can be used to generate a cleavage product F' which is selected such that it either hybridizes with the template nucleic acid C (path 1), with the template nucleic acid E (path 2) or with another template nucleic acid G (path 3).

Figure 1:
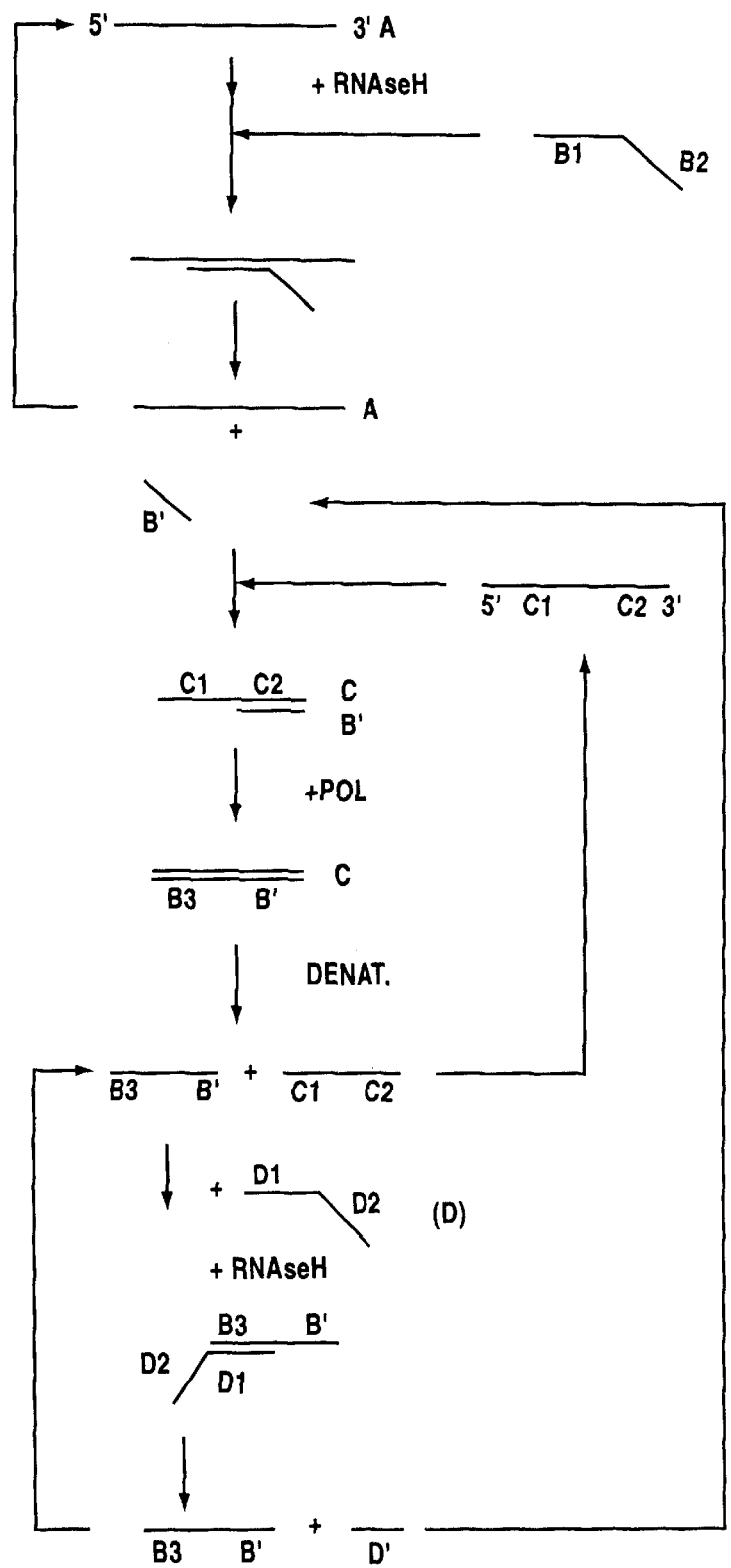
Figure 2:
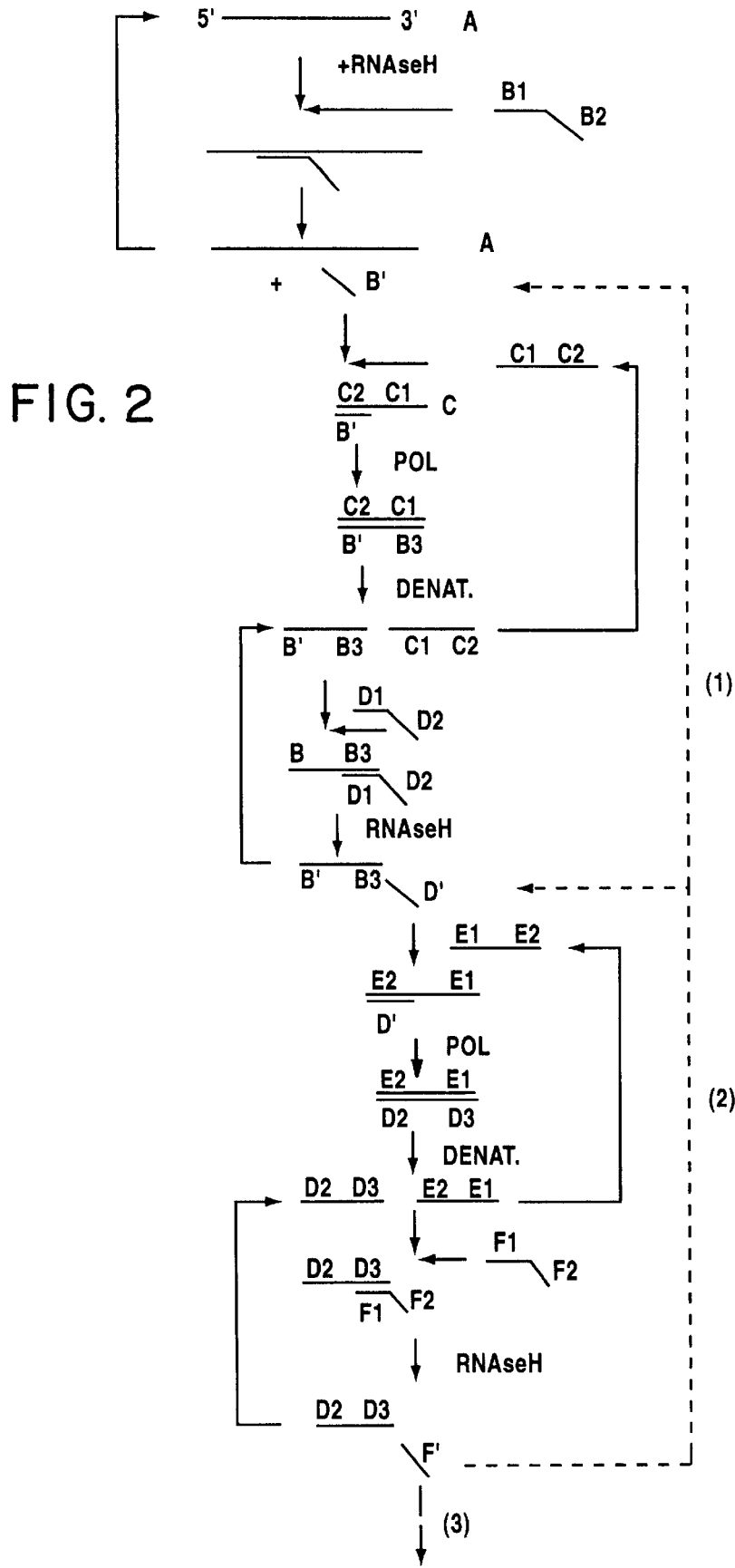

The steps shown in figures can be carried out successively while adding the respectively necessary reagents. It is, however, also possible to add all necessary components at the beginning of the reaction to have a simultaneously occurring process provided the components have been designed accordingly.

If denaturing of the template nucleic acid from the extension product is carried out in a thermal procedure, all non-thermostable components must be added again after the denaturing process. In this respect the use of a thermostable enzyme, e.g. Thermus-aquaticus-polymerase and thermostable RNase H is advantageous.

Target nucleic acid A can be detected owing to a product and/or intermediate product obtained in the amplification reaction. This is preferably done via detecting a label in at least one of the probe or template nucleic acids used or in a so-obtained cleavage or extension product. It is preferred that the template oligonucleotide with the cleavage product be reacted under suitable hybridization conditions together with the DNA polymerase and labelled deoxyribonucleoside triphosphates. The incorporation of labelled mononucleotides can, for example, be detected after separating the nucleic acids from non-reacted labelled deoxyribonucleoside triphosphates. When two differently labelled nucteotides are used, a direct solid phase-bound detection is possible.

The high degree of flexibility and the possible dual labelling, i.e. the simultaneous incorporation of differently labelled deoxynucleotides during the extension reaction, allow the use of the method on test strips or on microtiter plates and detection via flow-through cytometry or capillary electrophoresis.

If the sample does not contain any target nucleic acids, the template oligonucleotide hybridizes only with a chimeric RNA/DNA probe molecule. An extension of the probe molecule does not occur as the 3'-end does not hybridize with the template oligonucleotide.

The method of the invention is a detection method where both the extension product and the generated primer are reintroduced into the amplification cycle. Amplification cycle is understood to be a sequence of reactions, where a product of one reaction is again used to generate one or several of these products. In the drawing, these cycles are indicated by an arrow which leads back to an earlier reaction stage. This leads to an amplification with a theoretical amplification factor of more than $2^x$, if x represents the number of cycles. In this aspect, the method of the invention is hence superior to those methods based on PCR. Moreover, the amplification rate can even be further increased by a suitable design.

Subject matter of the invention is also a method for amplifying short nucleic acid sequences comprising the following steps:

a) extending the short nucleic acid sequences by an extension segment,
   b) hybridizing a longer nucleic acid sequence containing the sequence of the short nucleic acid (completely or partially) to the extension product in the extension area,
   c) digesting the longer nucleic acid to eliminate a part or all of the hybridized sequence,
   d) repeating steps a)–c) with the digestion products obtained in step c).

The short nucleic acid sequences are preferably the above mentioned primers or cleavage products. The longer nucleic acid sequence is preferably a probe nucleic acid and/or an amplification nucleic acid. The extension segment is, hence, preferably segment D3. The digestion of the longer nucleic acids preferably corresponds to the cleavage of the probe nucleic acids and/or the amplification probe in part B1 and/or D1 or F1. The repetition of steps a) to c) preferably corresponds to the cycle procedure of the cleavage products.

Another subject matter of the invention is a method for the sensitive detection of a target nucleic acid A by means of the following steps:

a) hybridizing the target nucleic acid A to a probe nucleic acid B containing a part B1 hybridizing with the target nucleic acid and containing a nucleic acid-specific part B2, b) cleaving the probe nucleic acid B in part B1,
c) hybridizing a cleavage product B' of the probe nucleic acid, said product containing the part B2 which does not hybridize with the target nucleic acid, with a template nucleic acid C containing a part C2 which hybridizes with a cleavage product B' in part B2 and also contains a part C1 which does not hybridize with part B1 of the probe nucleic acid,
d) extending the cleavage product B' by a nucleic acid part B3 which is completely or partially complementary to a part C1, and
e) hybridizing an amplification probe D to the extension product of cleavage products B' in part B3, the probe D containing a part D1 which is homologous to C1 or a part thereof and which can be cleaved.

In the above-mentioned method, the amplification probe D in part D1 is cleaved producing a cleavage product D'. The latter contains in a direct method a sequence which allows hybridization to the template nucleic acid C and extension analogous to the extension of B'. The amplification cycle would, hence, be closed. In a direct method, the amplification probe D also contains, in addition to part D1, a nucleic acid-specific part which is homologous to B2 or a part thereof It is particularly preferred that the nucleic acid-specific part B2 should not hybridize with the target nucleic acid. In a preferred manner, the hybrid of the extension product of cleavage product B' and template nucleic acid C is denatured between steps d) and e).

In a particularly preferred manner, the method when used as the above-mentioned indirect method also comprises the following steps:

f) cleaving the amplification probe D in part D1, preferably with the aid of RNAse H,
g) hybridizing the cleavage product D' with a template nucleic acid E which contains a part E2 that can be hybridized with the cleavage product in part D2 and also contains a part E1 which cannot be hybridized with part D1,
h) extending the cleavage product D' by a nucleic acid part D3 that is complementary to part E1, and optionally
i) hybridizing an amplification probe F with the extension product of cleavage product D' in part D3, said probe F containing a part F1 while F1 is homologous to C1 or a part thereof, or homologous to E1 or a part thereof, and F1 can be cleaved.

In this case, the amplification probe D is selected such that it contains a nucleic acid-specific part D2 in addition to part D1, said part D2 is, however, not homologous to B2 or part thereof. In a particularly preferred manner, part D2 is specific for a part E2 of the template nucleic acid E.

Another subject matter of the invention is a set of nucleic acids for the sensitive detection of target nucleic acids comprising a) a nucleic acid B with parts B1 and B2, wherein B1 is a part that is complementary to a part of the target nucleic acid and digestable as a hybrid with the target nucleic acid, and B2 is a nucleic acid-specific part,
b) a nucleic acid C with parts C1 and C2, wherein C1 is another nucleic acid-specific part and C2 is complementary to B2,
c) a nucleic acid D with a part D1, wherein D1 is homologous to C1 or a part thereof and can be cleaved.

In a preferred manner, the nucleic acid D also contains a part D2, which is homologous to B2 or a part thereof In other words, D2 is complementary to C2.

Yet another subject matter of the invention is a set of nucleic acids for the sensitive detection of nucleic acids, comprising a) a nucleic acid C with parts C1 and C2, wherein C1 is a nucleic acid-specific part, and C2 is another nucleic acid-specific part, wherein neither C1 nor C2 can hybridize with a target nucleic acid,
b) a nucleic acid D with parts D1 and D2, wherein D1 is homologous to C1 or a part thereof, and D2 is complementary to C2 or a part thereof.

This means that part D1 is complementary to part B3.

The sets in accordance with the invention can also contain reagents that are necessary for the detection, especially digesting enzymes, e.g. RNAse H, an enzyme to extend nucleic acids, e.g. a DNA-polymerase or reverse transcriptase, mononucleotides and buffers suitable for the enzymatic reactions.

The method of the invention is further illustrated in the following examples:

In the following examples, upper case letters are used in designated deoxyribonucleotide units, whereas lower case letters are used to designate ribonucleotide units.

EXAMPLE 1

Experimental procedure for radioactive detection 1 pmol of the RNA-DNA probe molecule
(B: 5'-GATCGGACTGGAAGTAATACGACTCACcga uacuaacauugagauucccg-3', SEQ.ID.NO. 1) is incubated with different amounts of the DNA to be detected (A: 5'-ATCTCGGGAATCTCAATGTTAGTATCGG-3', SEQ.ID.NO. 2) in a volume of 20 µl at 42° C. for 3 hours in buffer P2 (10 mM Hepes, 1 mM $MgCl_2$, pH 8.0) while adding 3 µg BSA, 20 U RNasin and 4 U RNase H. Then 1 pmol of the template oligonucdeotide (C: 5'-CGACGCCGCGTCGCAGAAGATCGGTGA GTCGTATTACTTCCAGTCCGATC-3', SEQ.ID.NO. 3) are added to the reaction mixture, which is heated up to 100° C. for 1 min, then immediately cooled on ice. Subsequently, 3 µl of 10×Taq buffer (100 mM Tris pH 8.3, 500 mM KCl, 15 mM $MgCl_2$, 1 mg/ml gelatin), dNTPs (final concentration 1 mM dATP, dCTP, dGTP, dTTP each) and 1 U Taq-polymerase are added to each mixture. The mixtures are then filled to a volume of 30 µl and incubated at 60° C. for 30 minutes. Then 10 pmol of the amplification probe which was radioactively labelled at its 5'-end via gamma-[32P]-ATP and polynucleotide kinase (D: 5'-GATCGGACTGGAAGTAATACGAC TCACcgccgcgucgcagaagauc-3', SEQ.ID.NO. 4) were added to the reaction mixtures. (*) Denaturing was repeated (1 min, 100° C.) and 4 U RNase H were added to the mixture which was then incubated for 3 hours at 42° C. Subsequently, another incubation step was carried out for 30 minutes at 60° C. This degradation reaction catalyzed by RNAse H as well as a Taq-DNA polymerase catalyzed elongation reaction were repeated twice beginning at (*).

For the detection reaction, the oligonucleotides (including the accumulated elongation products of cleavage product D' of the amplification probe, which were radioactively labelled at their 5'-ends) were placed on a 12% sequencing gel (Sambrook et al. (1989) Molecular Cloning, Cold Spring Harbour Laboratory Press, S.6.36 et seq.) and separated by means of electrophoresis. Autoradiography was used to identify the elongated primer D' and detect the presence of the target sequence A.

EXAMPLE 2

Experimental procedure of a non-radioactive detection:
10 pmol of the RNA-DNA probe molecule
(B: 5-GATCGGACTGGAAGTAATACGACTCACcg auacuaacauugagauucccg-3', SEQ.ID.NO. 1) are incubated with different amounts of the DNA to be detected (A: 5'-ATCTCGGGAATCTCAATGTTAGTATCGG-3', SEQ.ID.NO. 2) in a volume of 20 µl at 42° C. for 3 hours in buffer P2 (10 mM Hepes, 1 mM $MgCl_2$, pH 8.0) while adding 3 µg BSA, 20 U RNasin and 4 U RNase H. Then 10 pmol of the template oligonucleotide (C: 5'-CGACGCCGCGTCGCAGAAGATCGGTGA GTCGTATTACTTCCAGTCCGATC-3', SEQ.ID.NO. 3) are added to the reaction mixture, which is heated up to 100° C. for 1 min, then immediately cooled on ice. Subsequently, 3 µl of 10×Taq buffer (100 mM Tris pH 8.3, 500 mM KCl, 15 mM $MgCl_2$, 1 mg/ml gelatin), dNTPs (final concentration 1 mM dATP, dCTP, dGTP, DIG-dUTP, BIO-dUTP each) and 1 U Taq-polymerase are added to each mixture. The mixtures are then filled to a volume of 30 µl and incubated at 60° C. for 30 minutes. Then 100 pmol of the amplification probe which was radioactively labelled at its 5'-end via gamma-[32P]-ATP and polynucleotide kinase (D: 5'-GATCGGACTGGAAGTAATACGACTCACcg ccgcgucgcagaagauc-3', SEQ.ID.NO. 4) were added to the reaction mixtures. (*) Denaturing was repeated (1 min, 100° C.) and 4 U RNase H were added to the mixture which was then incubated for 3 hours at 42° C. Subsequently, another incubation step was carried out for 30 minutes at 60° C. This degradation reaction catalyzed by RNAse H as well as a Taq-DNA polymerase catalyzed elongation reaction were repeated twice beginning at (*).

Non-incorporated nucleotides are now separated by means of ethanol precipitation of the oligonucleotides. For the detection, the precipitated oligonucleotides (including the accumulated BIO-DIG-labelled elongation products) are dissolved in 210 µl buffer D (10 mM Hepes pH 8.3, 30 mM NaCl, 1 mM $MnCl_2$). Double labelled products are immobilized in a streptavidin-coated microtiter plate (MTP) (streptavidin-coated microtiter plate from the reverse transcriptase assay, non-radioactive, Boehringer Mannheim 1468 120). This is accomplished in that two portions of 100 µl each of the oligonucleotide solutions are pipetted into the wells of an MTP that were prewashed with washing buffer (0.5% (V/V) Tween 20 in PBS ("phosphate-buffered saline")). The MTP is incubated under shaking for 1 hour at 37° C. (Well-Warm1, manufactured by Denley Instruments GmbH).

The MTP containing the immobilized nucleic acid molecules is washed 5×with portions of 200 µl of washing buffer each time. Then there are added portions of 100 µl of the conjugate dilution (polyclonal <DIG>-S-Fab-PODpoly-conjugate (Boehringer Mannheim GmbH), 200 mU/ml in conjugate buffer (100 mM Na-phosphate pH 7.5, 0.9% (W/V) NaCl, 1% (WIV) Ralufon F4J or BSA Fraction V; the conjugate buffer is treated with diethylpyrocarbonate, sterile-filtered (0.2 µm-filter, manufactured by Nalgene) and stored at 4° C.)) and the MTP is again incubated under the same conditions.

Non-bound conjugate molecules are removed by washing 5 times. Now, 100 µl of the substrate solution (2,2'-azino-di-[3-ethylbenzthiezolinsulfonate(6)], ABTS) are added to each well. The colour reaction occurs at 37° C. under shaking. The optical density of the reacted ABTS is measured at 405 nm after brief shaking of the MTP immediately prior to the measurement in an ELISA reader (SLT) against the reference filter of 492 nm; after subtracting the zero-value (only ABTS), the mean values of the dual determination are obtained (SLT Easy-Base Version 4.01).

EXAMPLE 3

Experimental procedure when digoxigenin is incorporated
50 pmol of target-DNA A (5'-ATCTCGGGAATCTCAATGTTAGTATCGG-3', 28 mer, SEQ.ID.NO. 2) were incubated for a period of 3 hours at 42° C. with 50 pmol of RNA-DNA probe molecule B (5'-GATCGGACTGGAAGTAATACGACTCACcgauacu aacauugagauucccg-3', 50 mer, DNA-RNA-Oligo with 23 ribos at the 3'-end, SEQ.ID.NO. 1) and 4 µl 10×buffer (100 mM Tris-HCl, 50 mM Kcl, 15 mM $MgCl_2$, pH 8.3) in a volume of 40 µl while adding 6 µg BSA, 40 U RNasin and 4 U RNase H.

After incubation, 20 µl were removed for gel analysis and stopped with 2 µl stop buffer (6×TBE, 30% glycerine, bromophenol blue).

For the elongation reaction 25 pmol of template oligo C (5'-CGACGCCGCGTCGCAGAAGATCGGTGAGTCG TATTACTTCCAGTCCGATC-3', 50 mer, SEQ.ID.NO. 3) were added to the remaining 20 µl; this mixture was denatured for 1 min at 95° C. and immediately cooled on ice. After addition of 0.5 µl 10×buffer (see above), portions of 100 µM dATP, dCTP and dGTP, 65 µM of dTTP, 35 µM of DIG-dUTP (each final concentrations) and 2.5 U Taq-DNA polymerase, water was added to 25 µl. After incubation for 30 min at 60° C., the reaction was stopped with 3 µl of stop buffer (see above). The samples were added completely onto 20% polyacrylamide gel (Biometra-Minigel chamber).

Running buffer=1×TBE, running time approximately 1 h at 250 V.

Subsequently, the gel was stained in 1×TBE+EtBr (1 µg/ml). After visual examination under UV light, the gel was plotted onto a nylon membrane and UV-fixed.

The detection was carried out according to the standard procedure of the DIG system (Boehringer Mannheim GmbH).

Accordingly, a reaction without DIG-dUTP (with 100 µM dTTP) was run in parallel and the samples were applied onto a second gel. After electrophoresis and staining with EtBr, lane 6 was cut out of this gel and the DNA was eluted (in 20 µl TE buffer) according to Maniatis ("crush and soak" method according to Maxam and Gilbert, 1977).

Figure 3:
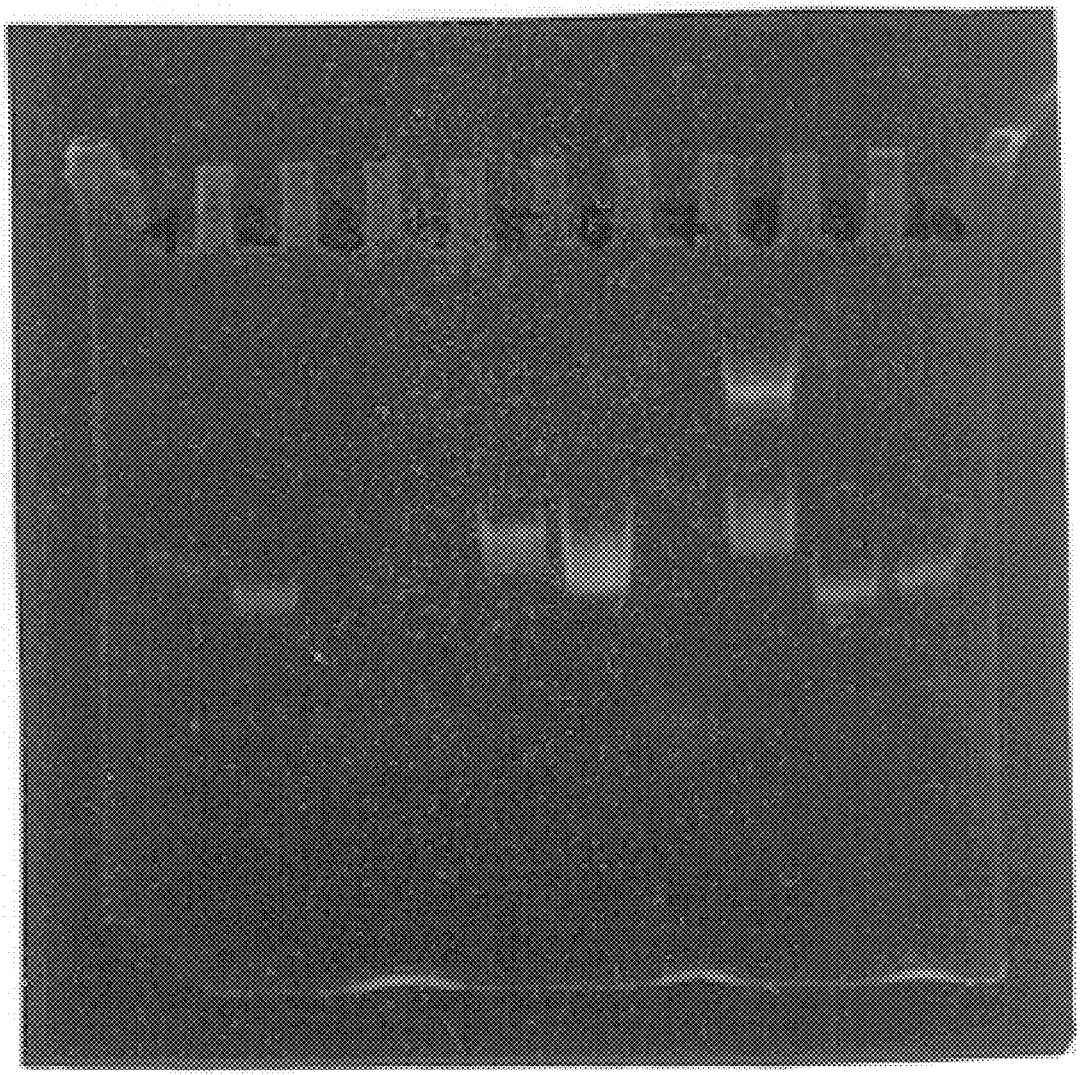
FIGS. 3 and 4 show gels with intermediate products of the reaction.

FIG. 3 shows the individual stages of the reaction (ethidium bromide staining).

Figure 4:
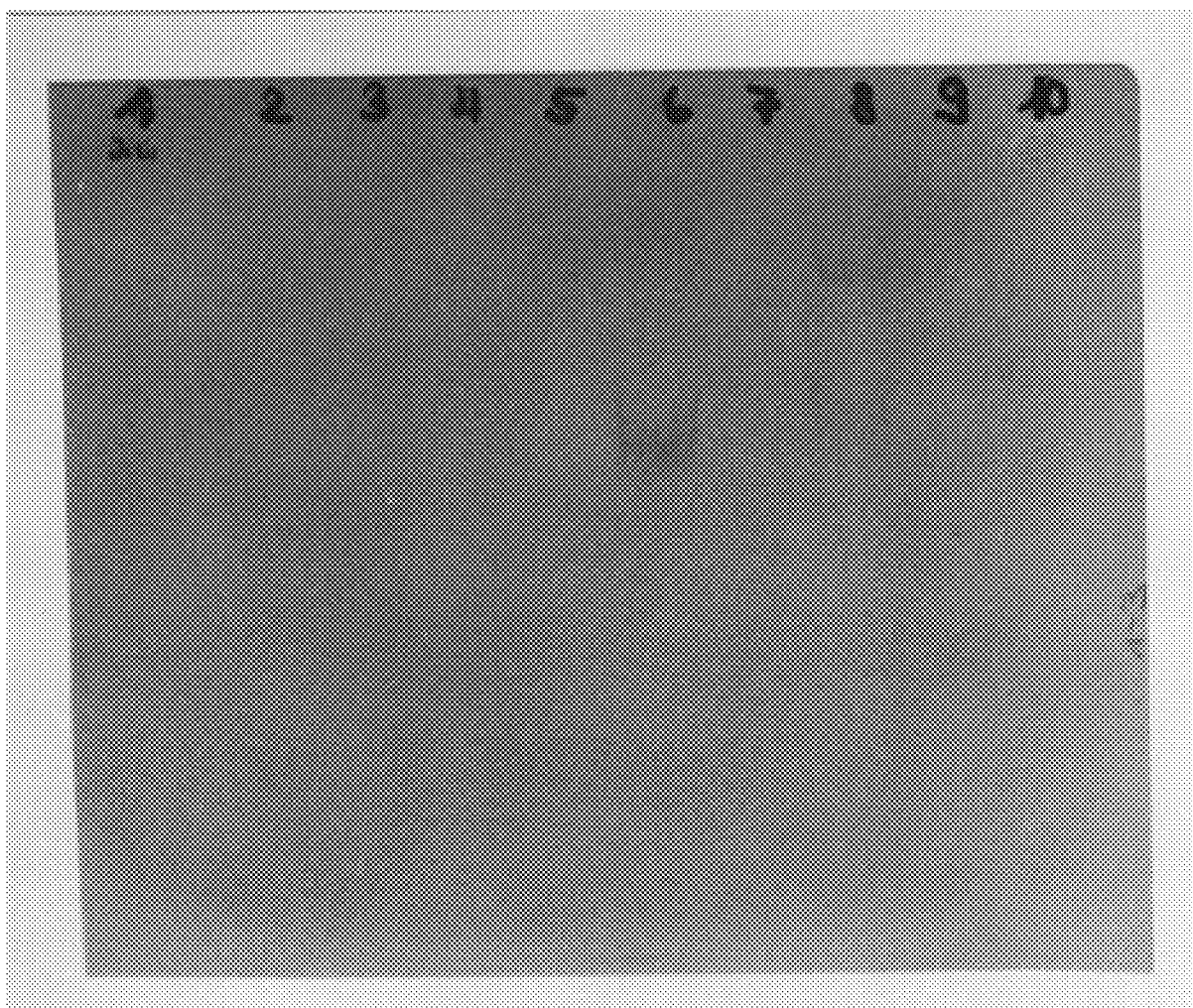

FIG. 4 shows the reaction products after blotting.

Lane 1: 25 pmol B  
Lane 2: 20 pmol C  
Lane 3: 25 pmol A + 25 pmol B + RNase H  
Lane 4: 25 pmol A + 25 pmol B + RNase H  
Lane 5: 25 pmol A + 25 pmol B without Rnase H  
Lane 6: as in 3 + 25 pmol C → filling reaction  
Lane 7: as in 4 → filling reaction (without C)  
Lane 8: as in 5 + 25 pmol C → filling reaction  
Lane 9: 25 pmol C → filling reaction  
Lane 10: 25 pmol C + 25 pmol A → filling reaction (filling reaction: Incubation with Taq-polymerase and dNTPs)

"Cycle" experiment 20 pmol of template C (SEQ.ID.NO. 3), 20 pmol of amplification probe D (5'-GATCGGACTGGAAGTAATACGACTCA Gcgccgcgucgcagaagauc-3', 46 mer, DNA-RNA-Oligo with 19 ribos on the 3'-end, SEQ.ID.NO. 4), 5 µl 10×buffer (see above), portions of 100 µM dATP, dCTP and dGTP, 65 µM dTTP, 35 µM DIG-dUTP (each final concentrations), 40 U RNasin, and 5 U thermostable RNase H and 2.5 U Taq-DNA-polymerase were added to 2 µl of the eluted DNA and the mixture was filled up to 50 µl. After denaturing for 3 minutes, the following cycle was repeated 10 times: 20 min 42° C.—10 min 60° C.—1 min 95° C.

After 1, 5 and 10 cycles, portions of 15 µl were removed for analysis and mixed with 2 µl stop buffer (see above).

The samples were applied onto a 20% polyacrylamide gel, running buffer=1×TBE, running time approximately 1 hour at 250 V.

Figure 5:
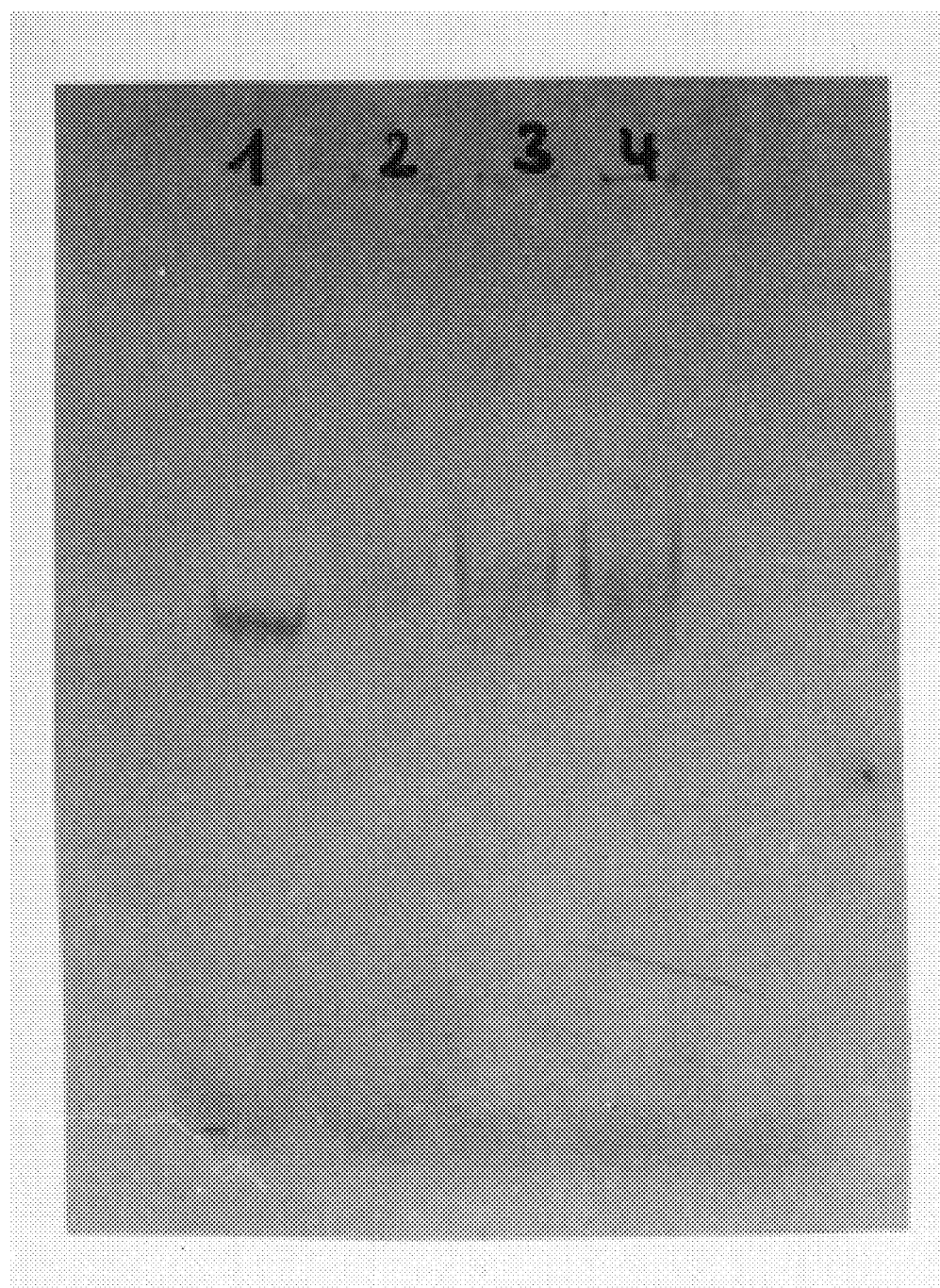
FIG. 5 shows the amplification products in the gel.

Subsequently, the gel was blotted on nylon membrane. After UV fixation, the blot was detected with anti-DIG-AP conjugate according to the standard procedure of the DIG system (FIG. 5).

Lane 1: DIG-labelled oligo, 46 mer (Length standard)

Lane 2: 1 cycle

Lane 3: 5 cycles

Lane 4: 10 cycles

We claim:

1. A set of nucleic acids for sensitively detecting a target nucleic acid A, comprising:
   a) a nucleic acid B comprising (1) a sequence B1 which is complementary to at least a part of the target nucleic acid A and (2) a sequence B2, wherein the nucleic acid B is cleaved using a digestive agent when the nucleic acid B is hybridized with the target nucleic acid A,
   b) a nucleic acid C comprising (1) a sequence C1 and (2) a sequence C2 which is complementary to at least a part of the sequence B2, and
   c) a nucleic acid D comprising (1) a sequence D1 which comprises a sequence which is the same sequence as at least a part of the sequence C1, wherein the nucleic acid D is cleaved using a digestive agent when the nucleic acid D is hybridized with the nucleic acid B.

2. The set of nucleic acids as claimed in claim 1, wherein the nucleic acid D further comprises (2) a sequence D2 which is complementary to at least a part of the sequence C2.

3. The set of nucleic acids as claimed in claim 1, wherein the sequence C1 and the sequence C2 do not hybridize to the target nucleic acid A,
   and wherein the nucleic acid D further comprises (2) a sequence D2 which is complimentary to at least a part of the sequence C2.

4. The set of nucleic acids as claimed in claim 3, wherein the sequence C1 and the sequence C2 do not hybridize to the target nucleic acid A under hybridization conditions wherein the nucleic acid B hybridizes with the target nucleic acid A.

5. A set of nucleic acids for sensitively detecting a target nucleic acid A, comprising:
   a) a nucleic acid C comprising (1) a sequence C1 and (2) a sequence C2, wherein the sequence C1 and the sequence C2 do not hybridize to the target nucleic acid A, and b) a nucleic acid D comprising (1) a sequence D1 which comprises a sequence which is the same sequence as at least a part of the sequence C1 and (2) a sequence D2 which is complementary to at least a part of the sequence C2.

6. A method of amplifying a first nucleic acid, comprising
   a) extending the first nucleic acid with an extension sequence to form an extension product;
   b) hybridizing a second nucleic acid with the extension product, wherein the second nucleic acid is longer than the first nucleic acid and comprises (i) a first sequence which base pairs with at least a part of the extension sequence and (ii) a second sequence which is the same as at least a part of the first nucleic acid, to form a hybrid between the first sequence and the at least a part of the extension sequence;
   c) thereafter digesting the first sequence of the second nucleic acid to produce single-stranded digestion products comprising the extension product and a cleavage product which comprises the second sequence of the second nucleic acid; and
   d) repeating steps a)–c) with the digestion products produced in step c).

7. The method of claim 6, wherein the second nucleic acid is 5–1000 nucleotides longer than the first nucleic acid.

8. The method of claim 6, wherein the second nucleic acid is 8–100 nucleotides longer than the first nucleic acid.

9. The method of claim 6, wherein the cleavage product comprises 12 nucleotides.

10. The method of claim 9, wherein the cleavage product is 12–35 nucleotides.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Oligodeoxyribonucleotide"

(ix) FEATURE:
        (A) NAME/KEY: misc_feature
        (B) LOCATION:1..27
        (D) OTHER INFORMATION:/note= "DNA"

(ix) FEATURE:
        (A) NAME/KEY: misc_feature
        (B) LOCATION:28..50
        (D) OTHER INFORMATION:/note= "RNA"

(xi) SEQUENCE DESCRIPTION: SEQ ID NO: 1:

GATCGGACTG GAAGTAATAC GACTCACCGA UACUAACAUU GAGAUUCCCG                50

(2) INFORMATION FOR SEQ ID NO: 2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Oligodeoxyribonucleotide"

(iii) HYPOTHETICAL: NO (xi) SEQUENCE DESCRIPTION: SEQ ID NO: 2:

ATCTCGGGAA TCTCAATGTT AGTATCGG                                       28

(2) INFORMATION FOR SEQ ID NO: 3:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Oligodeoxyribonucleotide"

(iii) HYPOTHETICAL: NO (xi) SEQUENCE DESCRIPTION: SEQ ID NO: 3:

CGACGCCGCG TCGCAGAAGA TCGGTGAGTC GTATTACTTC CAGTCCGATC                50

(2) INFORMATION FOR SEQ ID NO: 4:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligoribonucleotide"

```
        (iii) HYPOTHETICAL: NO (ix) FEATURE:
             (A) NAME/KEY: misc_feature
             (B) LOCATION:1..27
             (D) OTHER INFORMATION:/note= "DNA"

(ix) FEATURE:
             (A) NAME/KEY: misc_feature
             (B) LOCATION:28..46
             (D) OTHER INFORMATION:/note= "RNA"

(xi) SEQUENCE DESCRIPTION: SEQ ID NO: 4:

GATCGGACTG GAAGTAATAC GACTCACCGC CGCGUCGCAG AAGAUC                          46
```